United States Patent [19]
Seitz et al.

[11] Patent Number: 5,990,171
[45] Date of Patent: Nov. 23, 1999

[54] HYDRAZONOACETIC ACID AMIDES AND THE USE THEREOF AS PESTICIDES

[75] Inventors: Thomas Seitz, Langenfeld; Klaus Stenzel, Düsseldorf, both of Germany

[73] Assignee: Bayer Aktiengesellschaft, Leverkusen, United Kingdom

[21] Appl. No.: 08/945,293

[22] PCT Filed: Mar. 25, 1996

[86] PCT No.: PCT/EP96/01308

§ 371 Date: Sep. 25, 1997

§ 102(e) Date: Sep. 25, 1997

[87] PCT Pub. No.: WO96/31464

PCT Pub. Date: Oct. 10, 1996

[30] Foreign Application Priority Data

Apr. 5, 1995 [DE] Germany ................... 195 12 617

[51] Int. Cl.⁶ .................. A01N 31/16; C07C 243/12; C07C 231/02; C07C 233/00
[52] U.S. Cl. .................. 514/614; 514/451; 514/461; 514/475; 514/520; 514/529; 514/534; 514/599; 514/615; 549/356; 549/429; 549/512; 558/411; 560/24; 560/27; 560/29; 560/30; 560/45; 564/74; 564/147; 564/134; 564/142
[58] Field of Search ............... 564/147, 74, 134, 564/142; 514/614, 615, 599, 520, 529, 534, 451, 461, 475; 558/411; 560/45, 24, 27, 29, 30; 349/512, 429, 356

[56] References Cited

U.S. PATENT DOCUMENTS 5,461,049 10/1995 O'Brien et al. .

FOREIGN PATENT DOCUMENTS 2232449 1/1974 Germany .
9429267 12/1994 WIPO .

OTHER PUBLICATIONS

Shawali et al, Tetrahedron, pp. 2517–2528, 1971.
Popp et al, Notes pp. 473–475, 1971.
Chemical Abstracts, vol. 112, No. 8, Feb. 19, 1990, Abstract No. 57392, Hanna, M.A., et al. "Photoxidation retardants . . . derivatives".
Liebigs Ann. Chem. (1989), (12), 1271–4, Moderhack, Dietrich, "Ring Cleavage of . . . nucleophiles", p. 1271.
Chemical Abstracts, vol. 110, No. 21, May 22, 1989, Abstract No. 192697, El–Reedy, A.M., et al., "Reactions with monothiomalonaamides . . . thiazoles".
Chemical Abstracts, vol. 108, No. 9, Feb. 29, 1988, Abstract No. 75196, Mohareb, R.M., et al., "Polyfunctionally substituted . . . cyanoacetranilide".
Chemical Abstracts, vol. 95, No. 23, Dec. 7, 1981, Abstract No. 203515, Dubenko, R.G. et al., "Study of a series . . . salts".
Chemical Abstracts, vol. 93, No. 9, Sep. 1, 1980, Abstract No. 94934, Monguzzi, R. et al., "Synthesis and . . . acids".
Chemical Abstracts, vol. 87, No. 21, Nov. 21, 1977, Abstract No. 162131, Mahevskaya, M.S., "Synthesis and arylhdrazones".
Chemical Abstracts, vol. 80, No. 21, May 27, 1974, Moderhack, Dietrich, et al. "2–(N–Alkylhydroxylamino) acid . . . amides".
J. Heterocycl. Chem. (1971), 8(3), 473–5, Popp, Frank, et al., "Reaction of . . . amines".
Tetrahedron (1971), 27(12), 2517–28, Shawali, A.S.A.S., et al., "Synthesis and reaction . . . chlorides".
Chemical Abstracts, vol. 123, No. 25, Dec. 18, 1995, Abstract No. 339119, Frohberg, Petra, et al., "Lipoxygenase inhibitors . . . amidrazones".
English language translation of DE 2,232,449, 1974.

*Primary Examiner*—Shailendra Kumar
*Attorney, Agent, or Firm*—Sprung Kramer Schaefer & Briscoe

[57] ABSTRACT

The invention concerns hydrazonoacetic acid amides of general formula (I), a process for producing them, and the use of the said amides as pesticides. In the formula shown, the following meanings apply: A stands for a simple bond or optionally substituted alkylene; Q stands for oxygen or sulphur, $R^1$ stands for optionally substituted cycloalkyl, cycloalkenyl, aryl or heterocyclyl; $R^2$ stands for hydrogen or optionally substituted alkyl, cycloalkyl, cycloalkenyl, aryl or heterocyclyl; $R^3$ and $R^4$ are identical or different and each stand for hydrogen or optionally substituted alkyl or cycloalkyl; $R^2$ and $R^3$ together with the nitrogen atom to which they are bound form an optionally substituted heterocyclyl ring; $R^5$ stands for optionally substituted cycloalkyl, cycloalkenyl, aryl or heterocyclyl.

8 Claims, No Drawings

HYDRAZONOACETIC ACID AMIDES AND THE USE THEREOF AS PESTICIDES

This application is a 371 of PCT/EP96/01308, filed Mar. 25, 1996.

The invention relates to novel hydrazonoacetamides, to a process for their preparation and to their use as pesticides.

This invention provides novel compound of the general formula (I)

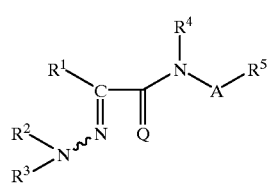

in which
A represents a single bond or optionally substituted alkylene,
Q represents oxygen or sulphur,
$R^1$ represents respectively optionally substituted cycloalkyl, cycloalkenyl, aryl or heterocyclyl,
$R^2$ represents hydrogen or respectively optionally substituted alkyl, cycloalkyl, cycloalkenyl, aryl or heterocyclyl,
$R^3$ and $R^4$ are identical or different and each represents hydrogen or respectively optionally substituted alkyl or cycloalkyl,
$R^2$ and $R^3$ join with the linking nitrogen atom to form an optionally substituted heterocyclyl ring,
$R^5$ represents respectively optionally substituted cycloalkenyl, cycloalkenyl, aryl or heterocyclyl.

In the definitions, the saturated or unsaturated hydrocarbon chains, such as alkyl, alkanediyl, alkenyl or alkinyl, including when combined with hetero atoms, as in alkoxy, alkylthio or alkylamino, are in each case straight-chain or branched.

Halogen generally represents fluorine, chlorine, bromine or iodine, preferably fluorine, chlorine or bromine, in particular fluorine or chlorine.

Aryl represents aromatic, mono or polycyclic hydrocarbon rings, such as, for example, phenyl, naphthyl, anthranyl, phenanthryl, preferably phenyl or naphthyl, in particular phenyl.

Heterocyclyl represents saturated or unsaturated and aromatic ring-shaped compounds in which at least one ring member is a hetero atom, i.e. an atom other than carbon. If the ring contains more than one hetero atom, these may be identical or different. Preferred hetero atoms are oxygen, nitrogen or sulphur.

Ring-shaped compounds optionally combine with further carbocyclic or heterocyclic, fused or bridged rings to form a polycyclic ring system. Preference is given to mono- or bicyclic ring systems, in particular to mono- or bicyclic aromatic ring systems.

Cycloalkyl represents saturated carbocyclic ring-shaped compounds which together with further carbocyclic, fused or bridged rings optionally form a polycyclic ring system.

Cycloalkenyl represents carbocyclic ring-shaped compounds which contain at least one double bond and which together with further carbocyclic, fused or bridged rings optionally form a polycyclic ring system.

Finally, it was found that the novel hydrazonoacetamides of the general formula (I) have very strong fungicidal activity.

The compounds according to the invention may be present as mixtures of different possible isomeric forms, in particular of stereoisomers, such as, for example, E and Z, threo and erythro, and optical isomers. What is described and claimed includes both the E and the Z isomers, and also the threo and erythro and the optical isomers and any mixtures of these isomers.

The invention preferably provides compounds of the formula (I) in which
A represents a single bond or represents alkylene having 1 to 6 carbon atoms which is optionally mono- or polysubstituted by identical or different substituents, the possible substituents preferably being selected from the list below:
halogen, cyano, nitro, amino, hydroxyl, formyl, carboxy, carbamoyl, thiocarbamoyl;
respectively straight-chain or branched alkoxy, alkylthio, alkylsulphinyl or alkylsulphonyl having in each case 1 to 6 carbon atoms; respectively straight-chain or branched alkenyl or alkenyloxy having in each case 2 to 6 carbon atoms;
respectively straight-chain or branched halogenoalkoxy, halogenoalkylthio, halogenoalkylsulphinyl or halogenoalkylsulphonyl having in each case 1 to 6 carbon atoms and 1 to 13 identical or different halogen atoms;
respectively straight-chain or branched halogenoalkenyl or halogenoalkenyloxy having in each case 2 to 6 carbon atoms and 1 to 13 identical or different halogen atoms;
respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 6 carbon atoms in the individual alkyl moieties;
cycloalkyl having 3 to 6 carbon atoms;
and aryl or heterocyclyl, each of which is optionally mono- or polysubstituted by identical or different substituents from
halogen, cyano and/or straight-chain or branched alkyl having 1 to 4 carbon atoms
and/or straight-chain or branched halogenoalkyl having 1 to 4 carbon atoms and 1 to 9 identical or different halogen atoms
and/or straight-chain or branched alkoxy or alkylthio having 1 to 4 carbon atoms
and/or straight-chain or branched halogenoalkoxy or halogenoalkylthio having 1 to 4 carbon atoms and 1 to 9 identical or different halogen atoms
and/or respectively doubly attached alkylene or dioxyalkylene having in each case 1 to 6 carbon atoms, each of which is optionally mono- or polysubstituted by identical or different substituents from halogen and/or straight-chain or branched alkyl having 1 to 4 carbon atoms and/or straight-chain or branched halogenoalkyl having 1 to 4 carbon atoms and 1 to 9 identical or different halogen atoms.
Q represents oxygen or sulphur,
$R^1$ represents aryl, cycloalkyl or cycloalkenyl having 3 to 7 carbon atoms, or heterocyclyl having 3 to 12 ring members, each of which is optionally mono- or polysubstituted by identical or different substituents, the possible substituents preferably being selected from the list below:
halogen, cyano, nitro, amino, hydroxyl, formyl, carboxy, carbamoyl, thiocarbamoyl; respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 8 carbon atoms in the individual alkyl moieties;

respectively doubly attached alkylene or dioxyalkylene having in each case 1 to 6 carbon atoms, each of which is optionally mono- or polysubstituted by identical or different substituents from the group consisting of halogen and straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

and aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents from halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy or alkylthio having 1 to 4 carbon atoms and/or straight-chain or branched halogenoalkoxy or halogenoalkylthio having 1 to 4 carbon atoms and 1 to 9 identical or different halogen atoms and/or respectively doubly attached alkylene or dioxyalkylene having in each case 1 to 6 carbon atoms, each of which is optionally mono- or polysubstituted by identical or different substituents from the group consisting of halogen and/or straight-chain or branched alkyl having 1 to 4 carbon atoms and/or straight-chain or branched halogenoalkyl having 1 to 4 carbon atoms and 1 to 9 identical or different halogen atoms.

$R^2$ represents hydrogen or represents alkyl having 1 to 4 carbon atoms or cycloalkyl having 3 to 6 carbon atoms, each of which is optionally mono- or polysubstituted by identical or different substituents from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which is optionally substituted by halogen) or represents optionally substituted phenyl, the possible substituents being selected from the list for $R^1$ above, $R^2$ and $R^3$ join with the linking nitrogen atom to form heterocyclyl which is in each case optionally mono- or polysubstituted by identical or different substituents from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl, $C_1$–$C_4$-alkyl (each of which is optionally substituted by halogen), $R^3$ and $R^4$ are identical or different and each represent hydrogen or represent alkyl having 1 to 4 carbon atoms or cycloalkyl having 3 to 6 carbon atoms, each of which is optionally mono- or polysubstituted by identical or different substituents from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$7alkylsulphonyl (each of which is optionally substituted by halogen), $R^5$ represents aryl, cycloalkyl or cycloalkenyl having 3 to 8 carbon atoms, or heterocyclyl having 3 to 12 ring members, each of which is optionally mono- or polysubstituted by identical or different substituents, the possible substituents preferably being selected from the list below:

halogen, cyano, nitro, amino, hydroxyl, formyl, carboxy, carbamoyl, thiocarbamoyl, respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 6 carbon atoms in the individual alkyl moieties;

respectively doubly attached alkylene or dioxyalkylene having in each case 1 to 6 carbon atoms, each of which is optionally mono- or polysubstituted by identical or different substituents from the group consisting of halogen and straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

and aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents from halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy or alkylthio having 1 to 4 carbon atoms and/or straight-chain or branched halogenoalkoxy or halogenoalkylthio having 1 to 4 carbon atoms and 1 to 9 identical or different halogen atoms and/or respectively doubly attached alkylene or dioxyalkylene having in each case 1 to 6 carbon atoms, each of which is optionally mono- or polysubstituted by identical or different substituents from the group consisting of halogen and/or straight-chain or branched alkyl having 1 to 4 carbon atoms and/or straight-chain or branched halogenoalkyl having 1 to 4 carbon atoms and 1 to 9 identical or different halogen atoms;

The invention in particular provides compounds of the formula (I) in which

A represents a single bond or represents methylene, 1,1-ethylene, 1,2-ethylene, 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), each of which is optionally mono- or polysubstituted by identical or different substituents from the group consisting of fluorine, chlorine, cyano and methoxy, Q represents oxygen or sulphur, $R^1$ represents respectively optionally mono- to trisubstituted cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the list below:

fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl;

cyclopropyl, cyclobutyl, cyclopentyl or cyclohexyl;

phenyl, benzyl, phenoxy, benzyloxy, each of which is optionally substituted by the abovementioned substituents;

$R^2$ represents hydrogen, methyl, ethyl, n- or i-propyl, n-, i-, s- or t-butyl or represents optionally substituted phenyl, the substituents being selected from the abovementioned list for $R^1$, $R^2$ and $R^3$ join with the linking nitrogen atom to form an optionally methyl-, ethyl-, methoxy- or ethoxy-substituted pyrrolidine, piperidine or morpholine ring, $R^3$ and $R^4$ are identical or different and each represent hydrogen or represent methyl, ethyl, n- or i-propyl, n-, i-, s- or t-butyl, $R^5$ represents respectively optionally mono- to trisubstituted cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the list below:

fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4diyl), methylenedioxy or ethylenedioxy, each of which is optionally mono- or polysubstituted by identical or different substituents from the group consisting of fluorine, chlorine, methyl, trifluoromethyl, ethyl, n- and i-propyl;

cyclopropyl, cyclobutyl, cyclopentyl or cyclohexyl.

Particular preference is given to compounds of the formula (I) in which

A represents a single bond or represents methylene, 1,1-ethylene, 1,2-ethylene, 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), each of which is optionally mono- or polysubstituted by identical or different substituents from the group consisting of fluorine, chlorine, cyano and methoxy, Q represents oxygen or sulphur, $R^1$ represents respectively optionally mono- to hexasubstituted cyclobutyl, cyclopentyl or cyclohexyl, preferred substituents being those listed below;

represents respectively optionally mono- to trisubstituted phenyl, naphthyl, furyl, benzofuranyl, thienyl, benzothienyl, pyridyl, quinolyl, tetrahydrofuryl or perhydropyranyl, the possible substituents preferably being selected from the list below:

fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, =methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4diyl), methylenedioxy or ethylenedioxy, each of which is optionally mono- or polysubstituted by identical or different substituents from the group consisting of fluorine, chlorine, methyl, trifluoromethyl, ethyl, n- and i-propyl; cyclopropyl, cyclopentyl, cyclohexyl; phenyl, phenoxy, benzyloxy, each of which is optionally substituted by the above-mentioned substituents;

$R^2$ represents hydrogen, methyl, ethyl, n- or i-propyl or represents optionally methyl-, ethyl-, chlorine-, fluorine-, methoxy-, ethoxy- or halogenomethoxy-substituted phenyl, $R^3$ represents hydrogen, methyl, ethyl, n- or i-propyl, $R^2$ and $R^3$ join with the linking nitrogen atom to form an optionally methyl-substituted pyrrolidine, piperidine or morpholine ring, $R^4$ represents hydrogen, represents methyl or represents ethyl, $R^5$ represents respectively optionally mono- to hexasubstituted cyclopropyl, cyclobutyl, cyclopentyl or cyclohexyl, preferred substituents being those listed below;

represents respectively optionally mono- to trisubstituted phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the list below:

fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl;

cyclopropyl, cyclobutyl, cyclopentyl or cyclohexyl.

A very particularly preferred group of compounds according to the invention is formed by those compounds of the formula (I) in which A represents a single bond or represents methylene, 1,1-ethylene, 1,2-ethylene, 1,1-propylene, 1,2-propylene, 1,3-propylene or 2,2-propylene, Q represents oxygen, $R^1$ represents phenyl, thienyl or furanyl, each of which is optionally mono- or disubstituted by bromine, chlorine, fluorine, nitro, methylsulphonyl, phenyl, phenyloxy, benzyloxy, cyclopropyl, cyclohexyl, methyl, ethyl, n- or i-propyl, n-, i-, s- or t-butyl, n-pentyl, n-hexyl, n-heptyl, methoxy, ethoxy, trifluoromethyl and/or methylthio or represents phenyl which is substituted by 3,4methylene- and ethylenedioxo, propane- 1,3-diyl and butane-1,4diyl, each of which is optionally substituted by fluorine or represents naphthyl, benzofuranyl or benzothienyl, $R^2$ represents hydrogen, methyl, ethyl or represents phenyl which is substituted by methoxy which is optionally substituted by methyl, chlorine, methoxy or fluorine, $R^3$ represents hydrogen, methyl or ethyl, $R^2$ and $R^3$ join with the linking nitrogen atom to form a pyrrolidine, piperidine or morpholine ring, $R^4$ represents hydrogen or methyl, $R^5$ represents cyclohexyl or optionally mono- to trisubstituted phenyl, thienyl, furyl, benzofuryl, benzothienyl, pyridyl, pyrimidyl, naphthyl, quinolyl, the possible substituents preferably being selected from the list below:

fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl, respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl.

Of very particular interest are compounds of the formula (I) in which the radical $R^1$ represents unsubstituted phenyl or phenyl which is substituted in position 3 and/or 4, or represents unsubstituted furanyl or thienyl or furanyl or thienyl which is substituted in position 4 and/or 5, the substituents being selected from the abovementioned group, in particular chlorine, bromine, fluorine, nitro, methylsulphonyl, phenyl, phenoxy, benzyloxy, cyclopropyl, cyclohexyl, methyl, ethyl, n-, i-propyl, n-, i-, -, t-butyl, n-pentyl, n-hexyl, n-heptyl, methoxy, ethoxy, methylthio and trifluoromethyl, or phenyl which is substituted by 3,4-methylene- and ethylenedioxo, propane-1,3-diyl and butane-1,4-diyl, each of which is optionally substituted by fluorine, or naphthyl, benzofuranyl or benzothienyl.

Particular preference is also given to compounds of the formula (I) in which $R^5$ represents phenyl which is substituted by methoxy in positions 3 and 4.

The abovementioned general or preferred radical definitions apply both to the end products of the formula (I) and, correspondingly, to the starting materials or intermediates required in each case for preparation.

These radical definitions can be combined with each other as desired, that is to say combinations between the ranges stated for preferred compounds are also possible.

Specific preferred compounds are listed in the tables below:

TABLE 1

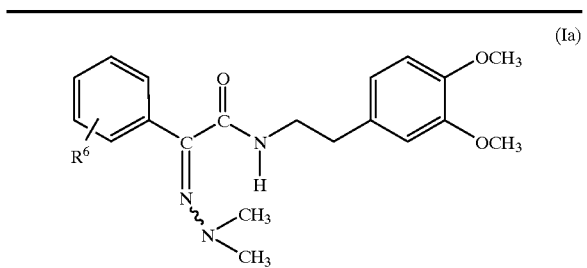

(Ia)

| Compound No. | R⁶ |
|---|---|
| Ia-1 | hydrogen |
| Ia-2 | 4-chloro |
| Ia-3 | 4-fluoro |
| Ia-4 | 4-bromo |
| Ia-5 | 4-methyl |
| Ia-6 | 4-ethyl |
| Ia-7 | 4-iso-propyl |
| Ia-8 | 4-n-propyl |
| Ia-9 | 4-n-butyl |
| Ia-10 | 4-iso-butyl |
| Ia-11 | 4-tert-butyl |
| Ia-12 | 4-sec-butyl |
| Ia-13 | 4-methoxy |
| Ia-14 | 4-ethoxy |
| Ia-15 | 4-methylthio |
| Ia-16 | 4-trifluoromethyl |
| Ia-17 | 3-chloro |
| Ia-18 | 3-fluoro |
| Ia-19 | 3-bromo |
| Ia-20 | 3-methyl |
| Ia-21 | 3-ethyl |
| Ia-22 | 3-iso-propyl |
| Ia-23 | 3-n-propyl |
| Ia-24 | 3-n-butyl |
| Ia-25 | 3-iso-butyl |
| Ia-26 | 3-tert-butyl |
| Ia-27 | 3-sec-butyl |
| Ia-28 | 3-methoxy |
| Ia-29 | 3-ethoxy |
| Ia-30 | 3-methylthio |
| Ia-31 | 3-trifluoromethyl |
| Ia-32 | 3,4-dichloro |
| Ia-33 | 3,4-difluoro |
| Ia-34 | 3,4-dibromo |
| Ia-35 | 3,4-dimethyl |
| Ia-36 | 3,4-diethyl |
| Ia-37 | 3,4-OCH₂O |
| Ia-38 | 3,4-OCH₂CH₂O |
| Ia-39 | 3,4-OCF₂O |
| Ia-40 | 3,4-OCF₂CF₂O |
| Ia-41 | 3,4-(CH₂)₃ |
| Ia-42 | 3,4-(CH₂)₄ |
| Ia-43 | 3,4-di-methoxy |
| Ia-44 | 3,4-diethoxy |
| Ia-45 | 3,4-dimethylthio |
| Ia-46 | 3,4-di-trifluoromethyl |
| Ia-47 | 3-chloro, 4-methyl |
| Ia-48 | 4-chloro, 3-methyl |
| Ia-49 | 3-chloro, 4-methoxy |
| Ia-50 | 4-chloro, 3-methoxy |
| Ia-51 | 3-chloro, 4-ethyl |
| Ia-52 | 4-chloro, 3-ethyl |
| Ia-53 | 3-methoxy, 4-ethoxy |
| Ia-54 | 4-methoxy, 3 ethoxy |
| Ia-55 | 3-methyl, 4-methoxy |
| Ia-56 | 4-methyl, 3-methoxy |
| Ia-57 | 3-methyl, 4-ethyl |
| Ia-58 | 4-methyl, 3-ethyl |
| Ia-59 | 3-methoxy, 4-ethyl |
| Ia-60 | 4-methoxy, 3-ethyl |
| Ia-61 | 4-nitro |
| Ia-62 | 4-methylsulphonyl |
| Ia-63 | 4-phenoxy |
| Ia-64 | 4-phenyl |

TABLE 1-continued

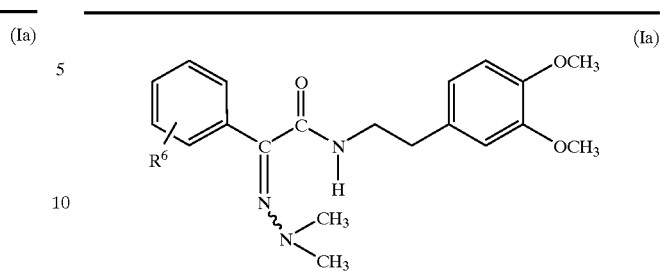

(Ia)

| Compound No. | R⁶ |
|---|---|
| Ia-65 | 4-benzyloxy |
| Ia-66 | 4-pentyl |
| Ia-67 | 4-hexyl |
| Ia-68 | 4-heptyl |
| Ia-69 | 4-cyclopropyl |
| Ia-70 | 4-cyclohexyl |

TABLE 2

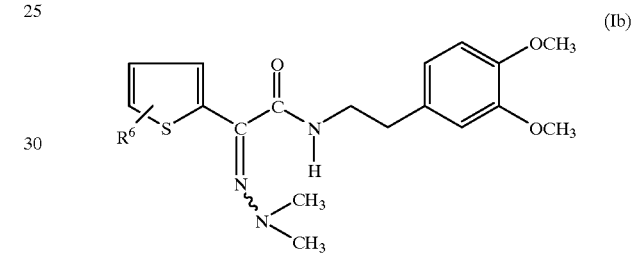

(Ib)

| Compound No. | R⁶ |
|---|---|
| Ib-1 | hydrogen |
| Ib-2 | 4-chloro |
| Ib-3 | 4-fluoro |
| Ib-4 | 4-bromo |
| Ib-5 | 4-methyl |
| Ib-6 | 4-ethyl |
| Ib-7 | 4-iso-propyl |
| Ib-8 | 4-n-propyl |
| Ib-9 | 4-n-butyl |
| Ib-10 | 4-iso-butyl |
| Ib-11 | 4-tert-butyl |
| Ib-12 | 4-sec-butyl |
| Ib-13 | 4-methoxy |
| Ib-14 | 4-ethoxy |
| Ib-15 | 4-methylthio |
| Ib-16 | 4-trifluoromethyl |
| Ib-17 | 5-chloro |
| Ib-18 | 5-fluoro |
| Ib-19 | 5-bromo |
| Ib-20 | 5-methyl |
| Ib-21 | 5-ethyl |
| Ib-22 | 5-iso-propyl |
| Ib-23 | 5-n-propyl |
| Ib-24 | 5-n-butyl |
| Ib-25 | 5-iso-butyl |
| Ib-26 | 5-sec-butyl |
| Ib-27 | 5-tert-butyl |
| Ib-28 | 5-methoxy |
| Ib-29 | 5-ethoxy |
| Ib-30 | 5-methylthio |
| Ib-31 | 5-trifluoromethyl |
| Ib-32 | 4,5-dichloro |
| Ib-33 | 4,5-difluoro |
| Ib-34 | 4,5-dibromo |
| Ib-35 | 4,5-dimethyl |
| Ib-36 | 4,5-diethyl |
| Ib-37 | 4,5-di-methoxy |

TABLE 2-continued

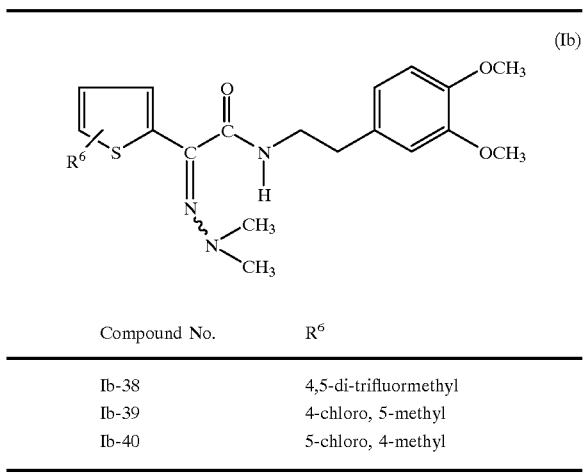
(Ib)

| Compound No. | $R^6$ |
|---|---|
| Ib-38 | 4,5-di-trifluormethyl |
| Ib-39 | 4-chloro, 5-methyl |
| Ib-40 | 5-chloro, 4-methyl |

TABLE 3

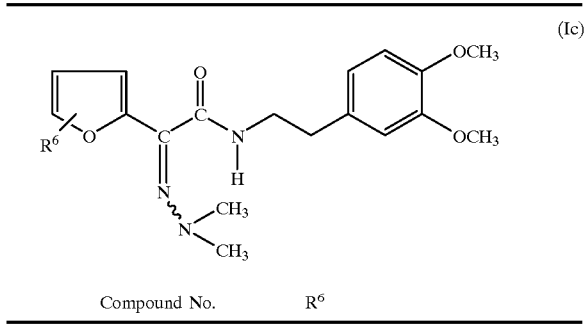
(Ic)

| Compound No. | $R^6$ |
|---|---|
| Ic-1 | hydrogen |
| Ic-2 | 4-chloro |
| Ic-3 | 4-fluoro |
| Ic-4 | 4-bromo |
| Ic-5 | 4-methyl |
| Ic-6 | 4-ethyl |
| Ic-7 | 4-iso-propyl |
| Ic-8 | 4-n-propyl |
| Ic-9 | 4-n-butyl |
| Ic-10 | 4-iso-butyl |
| Ic-11 | 4-tert-butyl |
| Ic-12 | 4-sec-butyl |
| Ic-13 | 4-methoxy |
| Ic-14 | 4-ethoxy |
| Ic-15 | 4-methylthio |
| Ic-16 | 4-trifluoromethyl |
| Ic-17 | 5-chloro |
| Ic-18 | 5-fluoro |
| Ic-19 | 5-bromo |
| Ic-20 | 5-methyl |
| Ic-21 | 5-ethyl |
| Ic-22 | 5-iso-propyl |
| Ic-23 | 5-n-propyl |
| Ic-24 | 5-n-butyl |
| Ic-25 | 5-iso-butyl |
| Ic-26 | 5-sec-butyl |
| Ic-27 | 5-tert-butyl |
| Ic-28 | 5-methoxy |
| Ic-29 | 5-ethoxy |
| Ic-30 | 5-methylthio |
| Ic-31 | 5-trifluoromethyl |
| Ic-32 | 4,5-dichloro |
| Ic-33 | 4,5-difluoro |
| Ic-34 | 4,5-dibromo |
| Ic-35 | 4,5-dimethyl |
| Ic-36 | 4,5-diethyl |
| Ic-37 | 4,5-di-methoxy |
| Ic-38 | 4,5-di-trifluoromethyl |

TABLE 3-continued

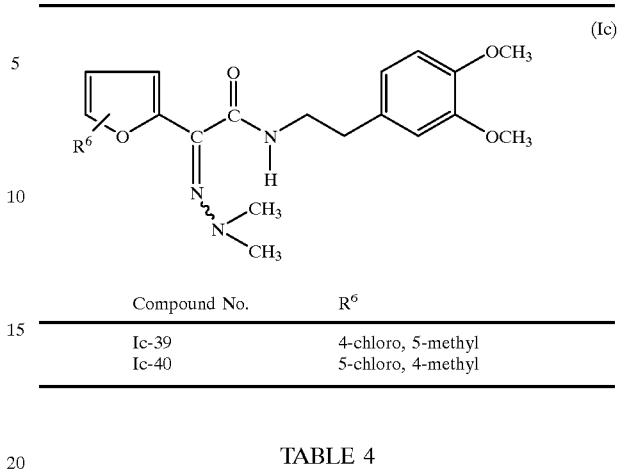
(Ic)

| Compound No. | $R^6$ |
|---|---|
| Ic-39 | 4-chloro, 5-methyl |
| Ic-40 | 5-chloro, 4-methyl |

TABLE 4

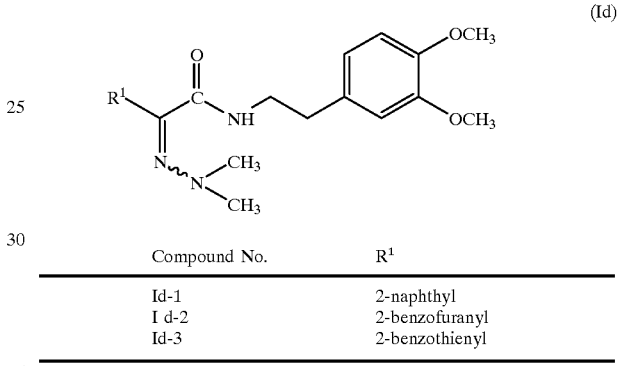
(Id)

| Compound No. | $R^1$ |
|---|---|
| Id-1 | 2-naphthyl |
| I d-2 | 2-benzofuranyl |
| Id-3 | 2-benzothienyl |

Table 5

Compounds Ia-1 to Id-3 corresponding to the formulae Ia, Ib, Ic and Id where the 3,4-dimethoxyphenyl group (generally denoted $R^5$) has been replaced by a phenyl radical carrying the substituents reported as $R^6$ for the compounds Ia-1 to Ia-70.

Table 6

Compounds Ia-1 to Id-3 corresponding to the formulae Ia, Ib, Ic and Id where the 3,4-dimethoxyphenyl group (generally denoted $R^5$) has been replaced by one of the following trisubstituted phenyl radicals:

substituents: 3,4,5-trimethoxy; 3,4,5-trichloro; 3,4,5-trimethyl.

Furthermore, it has been found that the novel hydrazonoacetamides of the general formula (I) are obtained when carboxylic acid derivatives of the general formula (II)

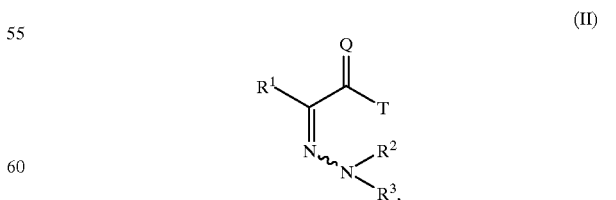
(II)

in which $R^2$, $R^2$, $R^3$ and Q are each as defined above and

T represents hydroxyl, halogen or alkoxy are reacted with an amine of the general formula (III)

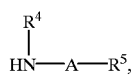

(III)

in which
R⁴, R⁵ and A are each as defined above
or with a hydrogen halide thereof
if appropriate in the presence of an acid acceptor, if appropriate in the presence of a condensing agent and if appropriate in the presence of a diluent.

Formula (II) provides a general definition of the carboxylic acid derivatives required as starting materials for carrying out the process according to the invention. In this formula (II), (Q, R¹, R² and R³) each preferably have in particular those meanings which have already been indicated in connection with the description of the compounds of the formula (I) according to the invention as preferred or as particularly preferred for (Q, R¹, R² and R³); T preferably represents alkoxy having 1 to 4 carbon atoms, in particular represents methoxy or ethoxy, represents hydroxyl or chlorine.

The starting materials of the formula (II) are known and/or can be prepared by known processes (cf. J. Heterocycl. Chem. (1990), 27(3), 487–95), Farmaco, Ed. Sci. (1980), 35(5), 394–404, Justus Liebigs Ann. Chem. (1969), 722, 38–44, Justus Liebigs Ann. Chem. (1969), 722, 29–37).

Formula (III) provides a general definition of the amines further to be used as starting materials.

The starting materials of the formula (III) are known organic chemicals for synthesis and/or can be prepared by methods known per se.

If appropriate, the process according to the invention is carried out in the presence of a suitable acid acceptor. Suitable acid acceptors are all conventional inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines, such as trimethylamine, triethylamine, tributylamine, N,N-dimethylanilin, N,N-dimethyl-benzylamine, pyridine, N-methylpiperidine, N,N-dimethylaminopyridine, diazabicyclooctane (DABCO), triazabicyclononene (DBN) or diazabicycloundecene (DBU).

If appropriate, the process according to the invention is carried out in the presence of a suitable condensing agent. Suitable condensing agents are all condensing agents which are conventionally used for such amidation reactions. Examples include acid halide formers such as phosgene, phosphorus tribromide, phosphorus trichloride, phosphorus pentachloride, phosphorus oxychloride or thionyl chloride; anhydride formers such as ethyl chloroformate, methyl chloroformate or methanesulphonyl chloride; carbodiimides, such as N,N'-dicyclohexyl-carbodiimide (DCC), or other conventional condensing agents, such as phosphorus pentoxide, polyphosphoric acid, N,N'-carbonyldiimidazol, 2-ethoxy-N-ethoxycarbonyl-1,2-dihydroquinoline (EEDQ) or triphenylphosphine/carbon tetrachloride.

If appropriate, the process according to the invention is carried out in the presence of a diluent. Suitable diluents for carrying out the process according to the invention are water and organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxan, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate, sulphoxides, such as dimethyl sulphoxide, alcohols, such as methanol, ethanol, n- or i-propanol, ethylene glycol, ethylene glycol monomethyl ether, ethylene glycol monoethyl ether, diethylene glycol monomethyl ether, diethylene glycol monoethyl ether, their mixtures with water or pure water.

When carrying out the process according to the invention, the reaction temperatures may be varied within a relatively wide range. In general, temperatures between −20° C. and +200° C., preferably temperatures between 0° C. and 150° C., are employed.

In the practice of the process according to the invention, generally 1 to 5 mol, preferably 1.0 to 2.5 mol, of amine are employed per mole of carboxylic acid derivative of the formula (II).

The reaction is carried out and reaction products are worked up and isolated according to known processes (cf. the Preparation Examples).

If appropriate, the process according to the invention is carried out in the presence of a catalyst. Examples include 4-dimethylaminopyridine, 1-hydroxy-benzotriazole and dimethylformamide.

When carrying out the process according to the invention, the reaction temperatures may be varied within a relatively wide range. In general, temperatures between −78° C. and +120° C., preferably temperatures between −60° C. and +25° C., are employed.

In the practice of the process according to the invention for preparing the compounds of the formula (I), generally 0.5 to 5 mol, preferably equimolar amounts, of amine of the formula (III) are employed per mole of the hydrazonoacetic acid derivative of the formula (II).

The reaction is carried out and the reaction products are worked up and isolated according to known processes (cf. the Preparation Examples).

The process according to the invention may also be carried out as a two-step process. For this purpose, the hydrazonoacetic acid derivatives of general formula (II) are initially converted into an activated form and reacted with the amines of the general formula (III) in a subsequent step to give the compounds of the general formula (I) according to the invention.

Suitable activated forms of the hydrazonoacetic acid derivatives of the formula (II) are all carboxy-activated derivatives, such as, for example, acyl halides, preferably acyl chlorides, acyl azides, further symmetric and mixed anhydrides, such as, for example, the mixed 0-alkylcarbonic anhydrides, furthermore activated esters, such as, for example, p-nitrophenyl esters or N-hydroxysuccinimide esters and adducts with condensing agents, such as, for example, dicyclohexylcarbodiimide or activated forms of the amino acids prepared in situ.

The active compounds according to the invention have potent microbicidal activity and are employed in practice for controlling undesirable microorganisms. The active compounds are suitable for use as crop protection agents, in particular as fungicides.

Fungicides are employed in crop protection for controlling Plasmodiophoromycetes, Oomycetes, Chytridiomycetes, Zygomycetes, Ascomycetes, Basidiomycetes and Deuteromycetes.

Some pathogens causing fungal diseases which come under the generic names listed above may be mentioned as examples, but not by way of limitation:

Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Peronospora species, such as, for example, *Peronospora pisi* or *Peronospora brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *Pyrenophora graminea* (conidial form: Drechslera, synonym: Helminthosporium);
Cochliobolus species, such as, for example, *Cochliobolus sativus* (conidial form: Drechslera, synonym: Helminthosporium);
Uromyces species, such as, for example, *Uromyces appendiculatus;*
Puccinia species, such as, for example, *Puccinia recondita;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;*
Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in viticulture, fruit-growing and vegetable-growing, for example against Plasmopara species and Phytophthora species.

Depending on their particular physical and/or chemical properties, the active compounds can be converted, if desired, to the customary formulations, such as solutions, emulsions, suspensions, powders, foams, pastes, granules, aerosols and microencapsulations in polymeric substances and in coating compositions for seeds, and ULV cold and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. In the case of the use of water as an extender, organic solvents can, for example, also be used as auxiliary solvents. Essentially, the following are suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water; liquefied gaseous extenders or carriers are to be understood as meaning liquids which are gaseous at ambient temperature and under atmospheric pressure, for example aerosol propellants such as halogenated hydrocarbons, or else butane, propane, nitrogen and carbon dioxide; suitable solid carriers are: for example, ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example, crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or, in their formulations, also as a mixture with known fungicides, bactericides, acaricides, nematicides or insecticides in order thus, for example, to widen the spectrum of action or to prevent development of resistance.

In many cases, synergistic effects are achieved.

Examples of possible co-components for mixtures are the following compounds:

Fungicides:

2-aminobutane; 2-anilino4-methyl-6-cyclopropyl-pyrimidine; 2',6'-dibromo-2-methyl-4'-trifluoromethoxy- 4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxy-phenyl)-acetamide; 8-hydroxyquinoline sulphate; methyl (E)-2-{2-[6(2-cyanophenoxy)-pyrimidin-4-yloxy]phenyl }-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157419, CGA 184699, chloethocarb, chlorethoxyfos, chloretoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lamda-cyhalothrin, lufenuron, malathion, mecarbam, mervinphos, mesulfenfos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, primiphos A, profenofos, profenophos, promecarb, propaphos, propoxur, prothiofos, prothiophos, prothoate, pymetrozin, pyrachlophos, pyraclofos, pyraclophos, pyradaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirirmphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, zetamethrin.

It is also possible to mix the active compounds according to the invention with other known active compounds, such as herbicides, or fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by wetting, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the treatment site.

PREPARATION EXAMPLE 1

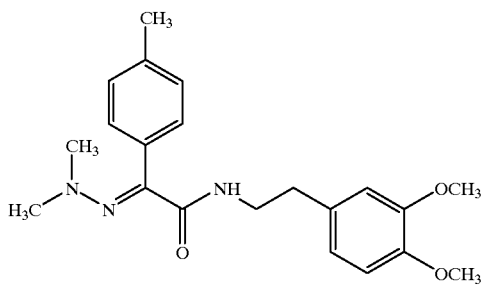

0.8 g (3.4 mmol) of ethyl 2-N,N-dimethyl-hydrazono-2-(4-methylphenyl)-acetate is initially charged in 10 ml of methanol and, at room temperature, 0.6 g (3.4 mmol) of 2-(3,4-dimethoxyphenyl)-ethylamine and 1.2 g (6.8 mmol) of 30% strength methanolic sodium methoxide solution are added in succession.

The mixture is stirred at 65° C. for 20 h, the solvent is then distilled off and the residue is taken up in methylene chloride and washed successively with water, dilute hydrochloric acid and water and dried over sodium sulphate. The solvent is distilled off and the crude product is chromatographed over silica gel using petroleum ether/ethyl acetate (10:1).

0.3 g (25% of theory) of N-[2-(3,4-dimethoxyphenyl)-ethyl]-2-N,N-dimethylhydrazono-2-(4-methylphenyl)acetamide is obtained.

$^1$H NMR (CDCl$_3$, TMS): δ=2.70 (S, 6H); 3.87 (S, 6H).

By the method of Example 1, and according to the procedures of the general description of the process, the compounds of the formula (Id) listed in Table 7 below are obtained:

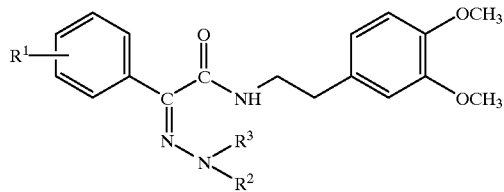

(Id)

TABLE 7

| No. | R$^1$ | R$^2$ | R$^3$ | E/Z | phys. const. |
|---|---|---|---|---|---|
| 2 | 4-CH$_3$ | Ph | H | E/Z | log p: 3.44/4.22 |
| 3 | 4-CH$_3$ | 4-CF$_3$O-Ph | H | E/Z | log p: 4.16/4.92 |
| 4 | 4-CH$_3$ | CH$_3$ | CH$_3$ | Z | log p: 2.94 |
| 5 | 4-CH$_3$ | CH$_3$ | CH$_3$ | E | log p: 2.61 |
| 6 | 4-Br | CH$_3$ | CH$_3$ | E/Z | log p: 2.78/3.14 |
| 7 | 4-C$_2$H$_3$ | CH$_3$ | CH$_3$ | E/Z | log p: 2.89/3.22 |
| 8 | 4-CH$_3$ | 4-CF$_3$OPh | H | E | log p: 4.93 |
| 9 | 4-CH$_3$ | 4-CF$_3$OPh | H | Z | log p: 4.16 |
| 10 | 4-Br | Ph | H | E/Z | log p: 3.64/4.50 |
| 11 | 4-C$_2$H$_5$ | Ph | H | E/Z | log p: 3.81/4.61 |
| 12 | 4-C$_2$H$_5$ | CH$_3$ | H | E/Z | log p: 3.15/3.42 |
| 13 | 4-Cl | CH$_3$ | CH$_3$ | E/Z | log p: 2.66/3.04 |
| 14 | 4-Br | CH$_3$ | CH$_3$ | E | log p: 2.77 |
| 15 | 4-Br | CH$_3$ | CH$_3$ | Z | log p: 3.14 |
| 16 | 3,4-(CH$_2$)$_4$ | CH$_3$ | CH$_3$ | E/Z | log p: 2.84/3.19 |
| 17 | 3,4-(CH$_2$)$_4$ | CH$_3$ | H | E/Z | log p: 2.75/3.13 |
| 18 | 3,4-(CH$_2$)$_4$ | Ph | H | E/Z | log p: 4.16/5.01 |
| 19 | 4-CH$_3$ | Ph | H | Z | log p: 4.21 |
| 20 | 3,4-(CH$_2$)$_3$ | CH$_3$ | H | E/Z | log p: 3.19/3.47 |
| 21 | 3,4-(CH$_2$)$_3$ | CH$_3$ | CH$_3$ | E/Z | log p: 2.43/3.36 |
| 22 | 3,4-(CH$_2$)$_3$ | Ph | H | E/Z | log p: 3.89/4.72 |
| 23 | 4-Br | CH$_3$ | H | E/Z | log p: 2.88/3.42 |
| 24 | 4-Cl | Ph | H | E/Z | log p: 3.54/4.38 |
| 25 | 4-Cl | CH$_3$ | CH$_3$ | Z | log p: 3.03 |
| 26 | 4-C$_2$H$_5$ | CH$_3$ | CH$_3$ | Z | log p: 3.32 |
| 27 | 3,4-(CH$_2$)$_3$ | CH$_3$ | CH$_3$ | Z | log p: 3.36 |
| 28 | 4-Cl | Ph | H | Z | log p: 4.38 |
| 29 | 4-Cl | (CH$_2$)$_5$ | | E/Z | log p: 4.16/5.01 |
| 30 | 3,4-(CH$_2$)$_4$ | CH$_3$ | CH$_3$ | Z | log p: 3.19 |
| 31 | 3,4-(CH$_2$)$_4$ | CH$_3$ | H | Z | log p: 3.73 |
| 32 | 3,4-(CH$_2$)$_3$ | Ph | H | Z | log p: 4.72 |
| 33 | 4-CH$_3$ | (CH$_2$)$_5$ | | E/Z | log p: 3.66/3.84 |
| 34 | 4-Br | Ph | H | Z | log p: 4.48 |
| 35 | 4-Br | Ph | H | E | log p: 3.60 |
| 36 | 3,4-(CH$_2$)$_4$ | CH$_3$ | H | E | log p: 2.75 |
| 37 | 4-Br | (CH$_2$)$_5$ | | E/Z | log p: 3.56/4.06 |
| 38 | 4-C$_2$H$_5$ | (CH$_2$)$_5$ | | E/Z | log p: 3.11/4.25 |
| 39 | 3,4-(CH$_2$)$_3$ | (CH$_2$)$_5$ | | E/Z | log p: 3.05/4.31 |
| 40 | 3,4-(CH$_2$)$_4$ | (CH$_2$)$_5$ | | Z | log p: 4.65 |
| 41 | 4-Br | (CH$_2$)$_2$O(CH$_2$)$_2$ | | E/Z | log p: 2.72/2.91 |
| 42 | 4-Cl | (CH$_2$)$_2$O(CH$_2$)$_2$ | | E/Z | log p: 2.62/2.80 |
| 43 | 3,4-(CH$_2$)$_4$ | (CH$_2$)$_2$O(CH$_2$)$_2$ | | E/Z | log p: 3.25/3.36 |
| 44 | 3,4-(CH$_2$)$_3$ | (CH$_2$)$_2$O(CH$_2$)$_2$ | | E/Z | log p: 2.93/3.07 |
| 45 | 3,4-(CH$_2$)$_3$ | (CH$_2$)$_4$ | | E/Z | log p: 2.92/3.15 |
| 46 | 3,4-(CH$_2$)$_4$ | (CH$_2$)$_4$ | | E/Z | log p: 3.25/3.50 |
| 47 | 3,4-(CH$_2$)$_4$ | (CH$_2$)$_2$O(CH$_2$)$_2$ | | Z | log p: 3.36 |
| 48 | 3,4-(CH$_2$)$_3$ | (CH$_2$)$_2$O(CH$_2$)$_2$ | | Z | log p: 3.07 |

Example A

Phytophthora test (tomato)/protective

Solvent: 4.7 parts by weight of acetone
Emulsifier: 0.3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated with an aqueous suspension of spores of *Phytophthora infestans*.

The plants are placed in an incubation cabinet at a relative atmospheric humidity of 100% and approximately 20° C.

Evaluation is carried out 3 days after the inoculation.

In this test, the compounds 1, 4, 14, 16, 17, 20, 29 and 31 according to the invention exhibit, at an active compound concentration of 100 ppm in the spray liquor, an efficacy of more than 80%.

Example B

Plasmopara test (vine)/protective

Solvent: 4.7 parts by weight of acetone
Emulsifier: 0.3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated with an aqueous suspension of spores of Plasmopara viticola and then remain in a humidity chamber at 20 to 22° C. and 100% relative atmospheric humidity for 1 day. Subsequently, the plants are kept in a greenhouse at 21° C. and 90% relative atmospheric humidity for 5 days. The plants are then moistened and kept for 1 day in a humidity chamber.

Evaluation is carried out 6 days after the inoculation.

In this test, the compounds 1, 4, 14, 16, 17, 20, 29 and 31 according to the invention exhibit, at an active compound concentration of 100 ppm in the spray liquor, an efficacy of more than 80%.

We claim:

1. A compound of the formula (I)

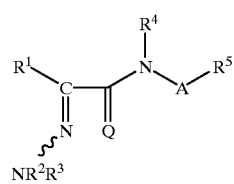

(I)

in which

A represents optionally substituted alkylene,

Q represents oxygen or sulphur, $R^1$ represents respectively optionally substituted cycloalkyl, cycloalkenyl, or aryl, $R^2$ represents hydrogewn or respectively optionally substituted alkyl, cycloalkyl, cycloalkenyl, or aryl, $R^3$ and $R^4$ are identical or different and each represents hydrogen or respectively optionally substituted alkyl or cycloalkyl, $R^5$ represents respectively optionally substituted cycloalkyl, cycloalkenyl, or aryl.

2. A compound of the formula (I) according to claim 1 in which

A represents alkylene having 1 to 6 carbon atoms which is optionally mono- or polysubstituted by identical or different substituents, the substituents being selected from the list below:

halogen, cyano, nitro, amino, hydroxyl, formyl, carboxy, carbamoyl, thiocarbamoyl;

respectively straight-chain or branched alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 6 carbon atoms in the individual alkyl moieties;

cycloalkyl having 3 to 6 carbon atoms;

and aryl which is optionally mono- or polysubstituted by identical or different substituents from halogen, cyano and/or straight-chain or branched alkyl having 1 to 4 carbon atoms;

and/or straight-chain or branched halogenoalkyl having 1 to 4 carbon atoms and 1 to 9 identical or different halogen atoms;

and/or straight-chain or branched alkoxy or alkylthio having 1 to 4 carbon atoms;

and/or straight-chain or branched halogenoalkoxy or halogenoalkylthio having 1 to 4 carbon atoms and 1 to 9 identical or different halogen atoms;

and/or respectively doubly attached alkylene or dioxyalkylene having in each case 1 to 6 carbon atoms, each of which is optionally mono- or polysubstituted by identical or different substituents from halogen and/or straight-chain or branched alkyl having 1 to 4 carbon atoms and/or straight-chain or branched halogenoalkyl having 1 to 4 carbon atoms and 1 to 9 identical or different halogen atoms;

Q represents oxygen or sulphur, $R^1$ represents aryl, cycloalkyl or cycloalkenyl having 3 to 7 carbon atoms, each of which is optionally mono- or polysubstituted by identical or different substituents, the substituents being selected from the list below:

halogen, cyano, nitro, amino, hydroxyl, formyl, carboxy, carbamoyl, thiocarbamoyl;

respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 8 carbon atoms in the individual alkyl moieties;

respectively doubly attached alkylene or dioxyalkylene having in each case 1 to 6 carbon atoms, each of which is optionally mono- or polysubstituted by identical or different substituents from the group consisting of halogen and straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

and aryl, aryloxy, arylthio, arylalkyl, arylalkyloxy or, arylalkylthio, each of which is optionally mono or polysubstituted by identical or different substituents from halogen, cyano and/or straight-chain or branched alkyl having 1 to 4 carbon atoms;

and/or straight-chain or branched halogenoalkyl having 1 to 4 carbon atoms and 1 to 9 identical or different halogen atoms;

and/or straight-chain or branched alkoxy or alkylthio having 1 to 4 carbon atoms;

and/or straight-chain or branched halogenoalkoxy or halogenoalkylthio having 1 to 4 carbon atoms and 1 to 9 identical or different halogen atoms;

and/or respectively doubly attached alkylene or dioxyalkylene having in each case 1 to 6 carbon atoms, each of which is optionally mono- or polysubstituted by identical or different substituents from the group consisting of halogen and/or straight-chain or branched alkyl having 1 to 4 carbon atoms and/or straight-chain or branched halogenoalkyl having 1 to 4 carbon atoms and 1 to 9 identical or different halogen atoms $R^2$ represents hydrogen or represents alkyl having 1 to 4 carbon atoms or cycloalkyl having 3 to 6 carbon atoms, each of which is optionally mono- or polysubstituted by identical or different substituents from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which is optionally substituted by halogen) or represents optionally substituted phenyl, the substituents being selected from the list for $R^1$ above, $R^3$ and $R^4$ are identical or different and each represent hydrogen or represent alkyl having 1 to 4 carbon atoms or cycloalkyl having 3 to 6 carbon atoms, each of which is optionally mono- or polysubstituted by identical or different substituents from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which is optionally substituted by halogen), $R^5$ represents aryl, cycloalkyl or cycloalkenyl having 3 to 8 carbon atoms, each of which is optionally mono- or polysubstituted by identical or different substituents, the substituents being selected from the list below:
halogen, cyano, nitro, amino, hydroxyl, formyl, carboxy, carbamoyl, thiocarbamoyl,
respectively straight-chain or branched alkyl, alkoxy, alkylthio, alkylsulphinyl or alkylsulphonyl having in each case 1 to 6 carbon atoms;
respectively straight-chain or branched alkenyl or alkenyloxy having in each case 2 to 6 carbon atoms;
respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
respectively straight-chain or branched halogenoalkenyl or halogenoalkenyloxy having in each case 2 to 6 carbon atoms and 1 to 13 identical or different halogen atoms;
respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 6 carbon atoms in the individual alkyl moieties; and
respectively doubly attached alkylene or dioxyalkylene having in each case 1 to 6 carbon atoms, each of which is optionally mono- or polysubstituted by identical or different substituents from the group consisting of halogen and straight-chain or branched alkyl having 1 to 4 carbon atoms and straight-chain or branched halogenoalkyl having 1 to 4 carbon atoms and 1 to 9 identical or different halogen atoms.

3. A compound of the formula (I) according to claim 1 in which

A represents methylene, 1,1-ethylene, 1,2-ethylene, 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), each of which is optionally mono- or polysubstituted by identical or different substituents from the group consisting of fluorine, chlorine, cyano and methoxy, Q represents oxygen or sulphur, $R^1$ represents respectively optionally mono- to trisubstituted cyclopropyl, cyclobutyl, cyclopentyl or cyclohexyl, phenyl or, naphthyl, the substituents being selected from the list below:

fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;
respectively doubly attached trimethylene (propane-1,3-diyl), tetramethylene (butane-1,4diyl), methylenedioxy or ethylenedioxy, each of which is optionally mono- or polysubstituted by identical or different substituents from the group consisting of fluorine, chlorine, methyl, trifluoromethyl, ethyl, n- and i-propyl;
cyclopropyl, cyclobutyl, cyclopentyl or cyclohexyl;
phenyl, benzyl, phenoxy, benzyloxy, each of which is optionally substituted by the abovementioned substituents;

$R^2$ represents hydrogen, methyl, ethyl, n- or i-propyl, n-, i-, s- or t-butyl or represents optionally substituted phenyl, the substituents being selected from the abovementioned list for $R^1$, $R^3$ and $R^4$ are identical or different and each represent hydrogen or represent methyl, ethyl, n- or i-propyl, n-, i-, s- or t-butyl, $R^5$ represents respectively optionally mono- to trisubstituted cyclopropyl, cyclobutyl, cyclopentyl or cyclohexyl, phenyl or, naphthyl, the substituents being selected from the list below:

fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;
respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl; and cyclopropyl, cyclobutyl, cyclopentyl or cyclohexyl.

4. A compound of the formula (I) according to claim 1 in which

A represents methylene, 1,1-ethylene, 1,2-ethylene, 1,1-, 1,2-, 1,3- or 2,2-propylene, 1,1-, 1,2-, 1,3-, 1,4, 2,2-, 2,3-butylene or 1,1-, 1,2- or 1,3-(2-methyl-propylene), each of which is optionally mono- or polysubstituted by identical or different substituents from the group consisting of fluorine, chlorine, cyano and methoxy, Q represents oxygen or sulphur, $R^1$ represents respectively optionally mono- to hexasubstituted cyclobutyl, cyclopentyl or cyclohexyl, the substituents being those listed below;

represents respectively optionally mono- to trisubstituted phenyl, or naphthyl, the substituents being selected from the list below:

fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl, methoxyiminoethyl or ethoxyiminoethyl; and respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl; cyclopropyl, cyclopentyl, cyclohexyl; phenyl, phenoxy, benzyloxy, each of which is optionally substituted by the abovementioned substituents;

$R^2$ represents hydrogen, methyl, ethyl, n- or i-propyl or represents optionally methyl-, ethyl-, chlorine-, fluorine-, methoxy-, ethoxy- or halogenomethoxy-substituted phenyl, $R^3$ represents hydrogen, methyl, ethyl, n- or i-propyl, $R^4$ represents hydrogen, represents methyl or represents ethyl, $R^5$ represents respectively optionally mono- to hexasubstituted cyclopropyl, cyclobutyl, cyclopentyl or cyclohexyl, the substituents being those listed below; or represents respectively optionally mono- to trisubstituted phenyl, or naphthyl, the possible substituents preferably being selected from the list below:

fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3diyl), tetramethylene (butane- 1,4diyl), methylenedioxy or ethylenedioxy, each of which is optionally mono- or polysubstituted by identical or different substituents from the group consisting of fluorine, chlorine, methyl, trifluoromethyl, ethyl, n- and i-propyl; and cyclopropyl, cyclobutyl, cyclopentyl or cyclohexyl.

5. A compound of the formula (I) according to claim 1 in which

A represents methylene, 1,1-ethylene, 1,2-ethylene, 1,1-propylene, 1,2-propylene, 1,3-propylene or 2,2-propylene, Q represents oxygen, $R^1$ represents phenyl, which is optionally mono- or disubstituted by bromine, chlorine, fluorine, nitro, methylsulphonyl, phenyl, phenyloxy, benzyloxy, cyclopropyl, cyclohexyl, methyl, ethyl, n- or i-propyl, n-, i-, s- or t-butyl, n-pentyl, n-hexyl, n-heptyl, methoxy, ethoxy, trifluoromethyl and/or methylthio or represents phenyl which is substituted by 3,4-methylene- and ethylenedioxo, propane-1,3-diyl and butane-1,4-diyl, each of which is optionally substituted by fluorine or represents naphthyl, $R^2$ represents hydrogen, methyl, ethyl or represents phenyl which is substituted by methoxy which is optionally substituted by methyl, chlorine, methoxy or fluorine, $R^3$ represents hydrogen, methyl or ethyl, $R^4$ represents hydrogen or methyl, $R^5$ represents cyclohexyl or optionally mono- to trisubstituted phenyl, or naphthyl, the substituents being selected from the list below:

fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl, and respectively doubly attached trimethylene (propane-1,3-diyl), tetramethylene (butane-1,4diyl), methylenedioxy or ethylenedioxy, each of which is optionally mono- or polysubstituted by identical or different substituents from the group consisting of fluorine, chlorine, methyl, trifluoromethyl, ethyl, n- and i-propyl.

6. Process for preparing compounds of the formula

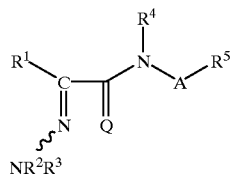 (I)

in which
A represents an optionally substituted alkylene,
Q represents oxygen or sulphur,
R$^1$ represents respectively optionally substituted cycloalkyl, cycloalkenyl, or aryl,
R$^1$, R$^3$ and R$^4$ are identical or different and each represent hydrogen or respectively optionally substituted alkyl,
R$^5$ represents respectively optionally substituted cycloalkyl, cycloalkenyl, or aryl,
characterized in that carboxylic acid derivatives of the general formula (II)

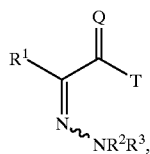 (II)

in which
R$^2$, R$^2$, R$^3$ and Q are each as defined above and
T represents hydroxyl, halogen or alkoxy
are reacted with an amine of the general formula (III)

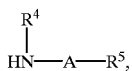 (III)

in which
R$^4$, R$^5$ and A are each as defined above
or with a hydrogen halide thereof
optionally in the presence of an acid acceptor, optionally in the presence of a condensing agent and optionally in the presence of a diluent.

7. A pesticidal composition comprising a diluent and a pesticidally effective amount of a compound of the formula (I)

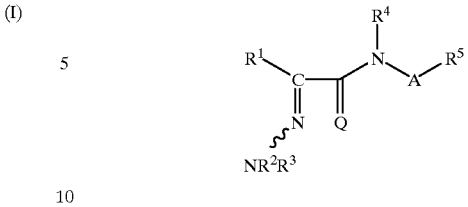 (I)

in which
A represents optionally substituted alkylene,
Q represents oxygen or sulphur,
R$^1$ represents respectively optionally substituted cycloalkyl, cycloalkenyl, aryl or heterocyclyl,
R$^2$ represents hydrogen or respectively optionally substituted alkyl, cycloalkyl, cycloalkenyl, or aryl,
R$^3$ and R$^4$ are identical or different and each represents hydrogen or respectively optionally substituted alkyl or cycloalkyl,
R$^5$ represents respectively optionally substituted cycloalkyl, cycloalkenyl, or aryl.

8. A method for controlling pests comprising administering to said pests and/or their habitat a pesticidally effective amount of a compound of the formula (I)

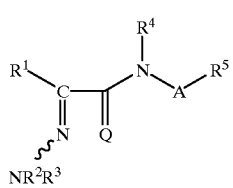 (I)

in which
A represents optionally substituted alkylene,
Q represents oxygen or sulphur,
R$^1$ represents respectively optionally substituted cycloalkyl, cycloalkenyl, aryl or heterocyclyl,
R$^2$ represents hydrogen or respectively optionally substituted alkyl, cycloalkyl, cycloalkenyl, or aryl,
R$^3$ and R$^4$ are identical or different and each represents hydrogen or respectively optionally substituted alkyl or cycloalkyl,
R$^5$ represents respectively optionally substituted cycloalkyl, cycloalkenyl, or aryl.

* * * * *